United States Patent [19]

Davis et al.

[11] Patent Number: 4,947,003

[45] Date of Patent: Aug. 7, 1990

[54] PROCESS FOR THE HYDROFORMULATION OF OLEFINICALLY UNSATURATED ORGANIC REACTANTS USING A SUPPORTED AQUEOUS PHASE CATALYST

[75] Inventors: Mark E. Davis; Juan P. Arhancet; Brian E. Hanson, all of Blacksburg, Va.

[73] Assignee: Virginia Tech Intellectual Properties, Inc., Blacksburg, Va.

[21] Appl. No.: 276,730

[22] Filed: Nov. 28, 1988

[51] Int. Cl.[5] .............................................. C07C 45/50
[52] U.S. Cl. ..................................... 568/454; 556/21; 556/136; 568/451; 568/492
[58] Field of Search ...................... 568/454, 451, 492; 260/429 R; 556/16, 21, 136

[56] References Cited

U.S. PATENT DOCUMENTS

| | | | |
|---|---|---|---|
| 3,855,307 | 12/1974 | Rony et al. | 568/454 |
| 4,157,313 | 6/1979 | Conan et al. | 568/454 |
| 4,193,942 | 3/1980 | Gerritsen et al. | 568/454 |
| 4,248,802 | 2/1981 | Kuntz | 568/454 |
| 4,334,101 | 6/1982 | Mantovani et al. | 568/454 |
| 4,348,539 | 9/1982 | Billig et al. | 568/454 |
| 4,356,125 | 10/1982 | de Munck et al. | 568/454 |
| 4,504,684 | 3/1985 | Fox et al. | 568/454 |

FOREIGN PATENT DOCUMENTS 1185453  3/1970  United Kingdom .

OTHER PUBLICATIONS

A. F. Borowski et al, "Water-Soluble Transition Metal Phosphine Complexes . . . ", Nouveau Journal De Chemie, vol. 2, No.2, p. 137.

L. A. Gerristen et al, "Hydroformylation with Supported Liquid Phase Rhodium Catalysts, Part I" J. Molecular Catalysis, 9 (1980) 139–155.

L. A. Gerritsen et al, "Hydroformulation with Supported Liquid Phase Rhodium Catalysts," Part II, J. Molecular Catalysis, 9 (1980) 157–168.

L. A. Gerritsen et al, "Hydroformulation with Supported Liquid Phase Rhodium Catalysts, Part 3," J. Molecular Catalysis, 9 (1980) 241–256.

L. A. Gerritsen et al, "Hydroformulation with Supported Liquid Phase Rhodium Catalysts, Part IV, " J. Molecular Catalysis, 9 (1980), 257–264.

L. A. Gerritsen et al, "Hydroformulation with Supported Liquid Phase Rhodium Catalysts, Part V," J. Molecular Catalysis, 9 (1980) 265–274.

N. A. de Munch et al, "Gas Phase Hydroformulation of Alkyl Alcohol with Supported Liquid Phase Rhodium Catalysts," J. Molecular Catalysis, 11 (1981) 233–246.

H. L. Pelt et al, "Hydroformulation of Alkenes with Supported Liquid Phase Rhodium Catalysts . . .", J. Molecular Catalysis, 31 (1985) 107–118.

H. L. Pelt et al, "Hydroformulation of Butene-1 and Butene-2 Over Rhodium–SLP Catalysts . . . , " J. Molecular Catalysis, 31 (1985) 371–383.

H. L. Pelt et al, "The Thermal and Chemical Stability Limits of Supported Liquid Phase Rhodium Catalysts in the Hydroformylation of Propene," J. Molecular Catalysis, 33 (1985) 119–128.

Primary Examiner—Werren B. Lone
Attorney, Agent, or Firm—Richard F. Lemuth

[57] ABSTRACT

A process for the hydroformylation of alkenes and other olefinically unsaturated reactants by reaction with carbon monoxide and hydrogen in the presence of a heterogeneous catalyst comprising a solid surface having immobilized thereon a solution of one or more rhodium complexes which is essentially immiscible with the organic reactant. Catalyst is subsequently recovered from the resulting hydroformylation product by one or more solid-liquid separation techniques.

26 Claims, No Drawings

PROCESS FOR THE HYDROFORMULATION OF OLEFINICALLY UNSATURATED ORGANIC REACTANTS USING A SUPPORTED AQUEOUS PHASE CATALYST

This invention relates to a catalytic process for the hydroformylation of olefinically unsaturated organic compounds, and more particularly to a process promoted by a catalyst system comprising a solution of a rhodium complex in a polar solvent, with said solution immobilized on a solid surface.

BACKGROUND OF THE INVENTION

Hydroformylation is a well known and commercially practiced process in which an olefinically unsaturated organic compound is contacted and reacted with a mixture of carbon monoxide and hydrogen, and thereby converted to a corresponding aldehyde or alcohol. In general, hydroformylation may be illustrated by the following equation:

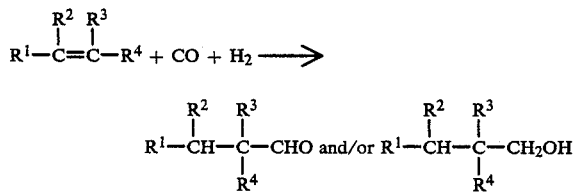

Frequently, hydroformylation is accompanied by some degree of isomerization of the carbon-carbon double bond position, resulting in several other aldehyde and alcohol structures in addition to those illustrated. In the above equation, each R represents, independently, an organic radical, or other substituent, e.g., a hydrogen or halogen atom, a hydroxyl group, a carbonyl group, a carboxyl group, etc, which does not interfere with the intended reaction at the double bond.

At present, rhodium catalyzed hydroformylation reactions are most commonly applied for the conversion of lower carbon number (e.g., $C_3$ to $C_5$) olefins to aldehydes, but are known to be applicable to the conversion of a wide range of other olefinically unsaturated reactants.

This invention most particularly relates to hydroformylation in the presence of a heterogeneous catalyst, comprising a rhodium complex supported on a solid surface. In conventional practice, hydroformylation reactions have, almost exclusively, utilized homogeneous rather than heterogeneous catalysts. The use of homogeneous catalysts for hydroformylation provides relatively high activity and selectivity at mild reaction conditions, but suffers from the difficulties inherent in the recovery of homogeneous catalysts from the reaction products. Because of the value of the metal, extremely effective catalyst recovery has been a necessity when dealing with homogeneous catalysts containing rhodium compounds and/or complexes. Moreover, the requirements for product purity have also been an important factor dictating effective catalyst removal from specialty chemical products of rhodium catalyzed hydroformylation. Procedures available in the art for recovery of homogeneous catalysts often prove to be difficult and/or expensive. In many cases, the requirements for catalyst recovery limit the commercial opportunities for the application of rhodium catalysts.

Although the difficulties inherent in the use of homogeneous hydroformylation catalysts have long provided incentive for the development of heterogeneous catalysts, attempts in the art to make use of heterogeneous rhodium catalysts have been largely unsuccessful, either because of leaching of rhodium from solid supports during the process or because of unacceptably low catalyst activity.

In other aspects, the present invention relates to a hydroformylation process carried out in the presence of a catalyst comprising a rhodium complex in a polar solvent (e.g., water) solution, which is essentially immiscible with the olefinically unsaturated organic reactant phase. U.S. Pat. No. 4,248,802 describes a catalytic system for hydroformylation which comprises a rhodium containing aqueous solution of certain sulfonated phosphine compounds. Rhodium is present either as metallic rhodium deposited on a support material, or in the form of water soluble compound or complex. The patent fails to teach or suggest a catalyst wherein a rhodium complex solution is supported on a solid. Nor do the teachings of this patent specify an aqueous rhodium complex solution which is essentially immiscible with the organic reactant phase. Instead, it is said to be of advantage in the process of U.S. Pat. No. 4,248,802 to add solvents (e.g., lower alcohols, ketones, nitriles and ethers) which increase the solubility of olefinic reactants in the aqueous catalyst solution.

Borowski et al (Nouveau, J. Chemie 2, 137 (1978)) also describe the preparation and use as hydroformylation catalysts of rhodium complexes dissolved in water. For hydroformylation, aqueous complex solutions are dispersed by mixing into an immiscible organic reactant phase. The publication does not contemplate immobilizing such complexes on solid support surfaces.

SUMMARY OF THE INVENTION

It has now been found that a heterogeneous catalyst comprising a rhodium complex in solution in a polar liquid phase immobilized on a solid surface effectively catalyzes the hydroformylation of olefinically unsaturated organic reactants.

Accordingly, the invention is a process for the hydroformylation of a liquid phase olefinically unsaturated organic reactant which comprises steps for
  a. contacting and reacting said organic reactant with a mixture of carbon monoxide and hydrogen, under hydroformylation conditions, in the presence of an effective amount of a heterogeneous catalyst comprising a solid surface having immobilized thereon a solution of one or more rhodium complexes in a polar solvent, said solution characterized as essentially immiscible with said organic reactant phase, and
  b. separating the catalyst from the resulting reaction mixture.

Use in this invention of a rhodium complex(es) immobilized on a surface of a solid support as specified provides a number of distinctions and benefits, relative to the catalysis of hydroformylation in prior art processes. For instance, the manner in which the rhodium complex is supported on the solid surface provides for an interfacial area between the immobilized polar liquid phase containing the rhodium complex(es) and the liquid organic reactant phase, which is significantly increased over the interfacial area associated with simple agitation of two free (unsupported) immiscible liquid phases. Furthermore, the separation of the active rhodium complex from the organic reactant by the interface between the polar and organic phases provides for modification of catalyst activity and selectivity. Still further, and perhaps most importantly, effective immobilization of a catalytically active rhodium complex on a solid support greatly facilitates practical application of the rhodium in, and its separation from, the hydroformylation reaction product.

The invention is preferably practiced with a catalyst wherein the polar solvent contains an amount of water at least equal to the water of hydration of the rhodium complexes present, and more preferably with a solvent which consists essentially of water.

DETAILED DESCRIPTION OF THE INVENTION

The present invention centers upon discoveries associated with the use in a hydroformylation process of a certain class of catalysts. Apart from the use of such catalysts, the process of the invention is, as a general rule, suitably conducted using such reactants and practicing under such processing procedures and reaction conditions as are known to the art for hydroformylation, particularly hydroformylation promoted by rhodium complex catalysts. Certain preferences may, however, be expressed for specific reactants, procedures and conditions.

Thus, for instance, the invention may be applied to the hydroformylation of organic reactant compounds having at least one site of olefinic unsaturation, that is at least one carbon to carbon double bond in the molecule. The olefin is necessarily unreactive with the water and/or other polar solvent(s) of the immobilized catalyst solution.

In certain preferred embodiments, the invention is preferably applied to the hydroformylation of olefinically unsaturated linkages in aliphatic (cyclic or acyclic) hydrocarbons. Monoolefins such as propylene, butylene, pentene, and hexene are a few examples of suitable lower alkene reactants. The invention is equally applicable to the hydroformylation of a broad range of alkenes, for instance, alkenes having from about 3 to about 30 carbon atoms, more preferably from about 3 to 25 carbon atoms. In practical terms, olefinic reactants of any carbon number, including those having a carbon numbers greater than 30, may be used as olefinic reactants in this process, to the extent that they are in the liquid state under process conditions. Solvents for the olefinic reactant may be used. The applicability of this invention to the higher carbon number olefins, e.g., $C_6$ and higher, offers substantial advantage over conventional homogeneous catalysts, which were generally limited in their application to lower olefins because of the procedures necessary for catalyst recovery. Feed hydrocarbons may include both branched and straight-chain compounds having one or more olefinic sites.

As is the case for conventional rhodium complex catalyzed hydroformylation, the process of this invention is similarly suitable for application to the hydroformylation at the olefinic bonds of non-hydrocarbons, again with the requirement that the reactants be in the liquid state under process conditions and the preferences for reactants in the carbon number range from about 3 to 30, particularly in the range from 3 to about 25. Thus, for instance, the invention is suitably utilized to hydroformylate olefinically unsaturated alcohols, aldehydes, acids, ketones, esters and other olefinic compounds having substituents the position and character of which do not negate the desired hydroformylation.

In the case reactant molecules having multiple double bonds, it is necessary to specify that they be non-conjugated. Thus, for instance, 1,5-hexadiene is suitable for hydroformylation under this invention, but 1,3-butadiene is not.

The unsaturated carbon-to-carbon bonds of the reactant may be at a terminal position in the molecule, as in 1-octene, or at an internal site, as in 4-decene or cyclohexene.

Macromolecular materials are also within the scope of suitable olefinically unsaturated reactants for purposes of this invention.

Mixtures of different olefinically unsaturated compounds are suitably present in the organic liquid reactant phase of the process and hydroformylated in the course of the invention. Depending upon the relative reactivities of the different olefinic compounds, some or all may undergo conversion to aldehydes and/or alcohols in the course of the process. Similarly, and again depending on their relative reactivities, one or more of the olefinic sites in (non-conjugated) polyolefins may be hydroformylated during practice of the invention.

It is critical to the practice of this invention that the liquid phase containing the olefinically unsaturated reactant (as well as hydroformylation products as they are formed, and possibly other compatible additives, solvents, etc.) be essentially immiscible with the polar phase of the supported catalyst. To the extent that the reactant phase may have a slight tendency to dissolve and remove polar solvent and/or ligand from the aqueous phase of the catalyst, solvent and/or ligand may be purposely incorporated into the reactant phase to counteract this tendency.

The requirement regarding immiscibility of the organic reactant phase dictates that the reaction system not contain additives, solvents or other components of such a nature and in such a quantity that they promote a meaningful degree of miscibility between the aqueous catalyst phase and the organic reactant phase. This is in distinction to prior art hydroformylation processes which have utilized organic co-solvents, phase-transfer agents, and the like, e.g., lower alcohols, to increase solubility between polar catalyst phases and organic reactants.

As in conventional hydroformylation, the olefinically unsaturated reactant is contacted with a mixture of carbon monoxide and hydrogen. As is generally known for such hydroformylation processes, water may be introduced to serve as the source of the hydrogen reactant.

Commonly, although by no means necessarily, the $H_2/CO$ mixture is present in the hydroformylation reactor in a stoichiometric excess (for example, from about 1 to 10 times that required), relative to the olefinically unsaturated reactant (taking into account the number of double bonds in that reactant which it is desired to convert), and has a molar excess of hydrogen to carbon monoxide (for example, a molar ratio of $H_2:CO$ in the range from about 1 to 10). However, neither the total quantity of the $CO/H_2$ mixture, relative to the quantity of olefinic reactant compounds, nor the ratio of CO and $H_2$ within this mixture is critical to the practice of this invention, and both can be varied as desired (and according to principles well known in the art) to control reaction rate and yield of desired product. As is recognized, each conversion to alcohol requires one molecule of CO and two molecules of $H_2$ for each double bond site converted. When producing aldehydes, the reaction consumes one molecule of CO and one of $H_2$ for each double bond converted.

The olefinically unsaturated reactant is necessarily contacted with the carbon monoxide and hydrogen mixture, under hydroformylation reaction conditions, in the presence of a quantity of the specified immobilized polar phase catalyst which is sufficient to promote the desired hydroformylation.

Suitable supported polar phase catalysts comprise a polar solvent solution of a rhodium complex, immobilized on a solid surface. As used herein, the term "complex" is understood to indicate a combination of a metal atom, particularly a rhodium atom, with one or more electronically-rich "ligand" molecules or atoms capable of independent existence. Conversely, the "ligand" has a pair of electrons capable of bonding with the metal atom and forming the complex. The term "immobilized" as used in describing the invention refers to the action of chemical or physical forces which prevent the rhodium complex(es) in the polar solution of the catalyst from migrating into the organic reactant phase.

For immobilization of the polar solvent solution of the rhodium complex, the solid surface is necessarily one which is compatible with a partial or complete covering by the polar solution. Many of the ligands preferred for forming the water soluble rhodium complex are surface active and promote wetting of the solid surface by the solution. In addition, the solid must be one which retains its structural integrity in the presence of the polar catalyst solution and the organic reactant phase. Suitable solid surfaces are exemplified by silicas, aluminas, titanias, aluminophosphates, carbon, polymers, and compacted clays.

Although not in principle necessary to the practice of this invention, a porous solid is preferred in order to provide greater surface area for interface with the organic reactant phase. It has further been observed that, with porous supports having a broad distribution in pore sizes, the polar solution of the catalyst does not distribute uniformly over the surface but instead preferentially distributes into the smaller pores. As a result, a relatively thick film of the aqueous phase may block access of the organic reactant into these smaller pores, while the surfaces of the larger pores are incompletely loaded or covered with the aqueous phase. For such reasons, a solid porous support characterized by pores of relatively uniform diameter is more preferred. Examples of narrow pore size distribution supports include high silica glasses which are commercially available with mean pore diameters in the range from about 70 to 3,000 Å. Preferably, the pores of a porous support are predominantly of a diameter greater than about 20 Å.

Without intention that the invention be limited to one theory or mechanism of operation, it is thought that the hydroformylation occurs at the interface between the two essentially immiscible phases: (1) the organic reactant phase and (2) the supported polar phase of the catalyst. A catalyst according to the invention, having an aqueous phase supported on the surface of a solid, provides an interfacial area between the organic reactant and the aqueous phase which is significantly increased over that which could be reasonably expected from simple agitation of two immiscible phases.

Examples of suitable polar solvents for the rhodium complex include water and aqueous solutions of other polar solvents, for instance one or more other solvents selected from the group consisting of (poly)alkylene glycols, alcohols, diols, polyols and the like. In general, the solvent must be one in which the rhodium complex has appreciable solubility, and one which is essentially immiscible with the olefinically unsaturated reactant (and, as it is formed, the hydroformylation product) phase.

It is considered necessary to the invention that the polar rhodium complex solution of the catalyst contain as least some water, particularly at least that amount of water which corresponds to the water of hydration of the rhodium complex. Preferably, the polar solvent contains water in a major portion, by weight; more preferably the solvent consists essentially of water. The use of a solvent consisting of water is considered most preferred.

A variety of rhodium complexes are known in the art to catalyze the hydroformylation of olefinically unsaturated organic reactants. In general, however, prior art catalytic complexes are formed from ligands tailored to promote the solubilization of the rhodium complex in the organic reactant and product phase. For purposes of this invention, however, the ligand is necessarily one which is instead preferentially soluble in the polar phase of the supported catalyst and preferably one which is essentially insoluble in the organic reactant phase.

Rhodium complexes which are soluble in water and other polar solvents are known in the art. Typically, the complex is formed from a ligand, for instance, a tertiary alkyl or aryl phosphine ligand, wherein one or more of the alkyl or aryl groups have been "functionalized" by addition of one or more substituents (e.g., one or more carbonyl, carboxyl, nitro, amino, hydroxy, sulfonate, phosphate, sulfate, ether, polyether, or quaternary ammonium groups) to aid in their solubilization in polar solvents.

Rhodium complexes are formed upon contact of the ligand with a rhodium complex or salt, such as, for example, rhodium carbonyl, rhodium chloride, or rhodium diamine.

One particularly preferred class of water soluble rhodium complexes are those derived from sulfonated phosphine ligands as described in the aforementioned U.S. Pat. No. 4,248,802. The disclosures of this patent relevant to rhodium complexes and their preparation are incorporated herein by this reference.

While the concentration of the rhodium complex(es) in the immobilized polar solution of the catalyst is not critical to the invention, a solution having a relatively high concentration of the complex(es) is desirable from the standpoint of higher catalyst activity. Moreover, the complex(es) are considered less stable in solutions of lesser concentration. A catalyst containing a quantity of immobilized rhodium complex which is greater than the limit of the solubility of the rhodium complex in the available polar solvent (that is, a catalyst containing the complex both in solution in the polar solvent and also as a separate undissolved component immobilized on the solid) is very suitable. In any event, however, the catalyst must contain an activating amount of water, that is, an amount which is equal to or greater than that corresponding to the water of hydration of the complex. The presence of the polar solvent in at least an activating amount results in an increase in catalytic activity, relative to the activity of catalysts which do not comprise a distinct aqueous solution immobilized on the solid. Typically, the catalyst is activated by the presence in the immobilized catalyst solution of a quantity of polar solvent which is about 10 percent or more by weight, relative to the quantity of the rhodium complex present. The optimum concentration of the rhodium complex in the solution will depend upon the choice of a particular ligand.

The catalyst used in the process of this invention is catalytically effective even in relatively small amounts. Thus, for instance, a batch reaction according to the invention is, in general, suitably carried out with a quantity of catalyst containing as little as about 0.00001 parts by weight of rhodium (calculated as the metal) per each part by weight of the olefinically unsaturated reactant. Quantities of catalyst containing at least about 0.0001 parts by weight of rhodium, calculated on this basis, are considered particularly preferred.

In one preferred method for making catalysts for use in this invention, the solid surface is initially impregnated with the rhodium complex, followed by addition of sufficient polar solvent to dissolve all or part of the complex, thereby forming a solution which coats, in whole or part the available solid surface area. For the initial impregnation, the complex can, for instance, be introduced into the pores of a porous solid as a solution in any convenient solvent. Removal of this solvent by evaporation under relatively mild conditions, and preferably under vacuum, deposits the complex over the external and pore surfaces. Polar solvent for the final complex solution can then be added in a controlled manner, for instance, as a vapor which condenses on the surface and dissolves, in whole or in part, the rhodium complex(es). This two step approach to immobilization of the complex solution on the solid surface, has advantage over a one step process alternative, in which the solid is coated directly with the rhodium complex solution in the polar solvent. In a one step impregnation and immobilization, it is in many cases difficult to control the uniformity of the distribution of the solution over the solid surface, particularly over the surface of a porous solid. However, catalysts prepared by a one step, direct immobilization procedure come within the scope of this invention, as do catalysts prepared by other alternatives for immobilization as will be apparent to those skilled in the art.

When loading the polar solution onto the solid surface, or, equivalently, when forming the solution on the solid surface, it is preferred that care be taken to maintain a loading which does not result in filling or blocking of the pores of a porous solid catalyst component and thus decreasing the effective interfacial area between the polar and organic phases. Preferably, the solution loading is such that the finished catalyst maintains high interfacial surface area between a film of the polar solution on the solid and the organic phase. However, the invention is also considered to encompass catalysts in which the immobilized solution fills the pore volume of a porous support.

Suitable hydroformylation conditions for purposes of the invention correspond to those of prior art hydroformylation processes catalyzed by rhodium complexes, and include, for example, temperatures in the range from about 50° C. to about 250° C. and pressures in the range from about 1 to 200 atm. Preferably, process temperature is in the range from about 50° C. to about 150° C., while a temperature in the range from about 70° C. to about 140° C. and a pressure in the range from about 0 to 2000 psig is considered more preferred. Care must be taken to operate at sufficiently low temperature and sufficiently high pressure to maintain the polar solvent of the rhodium complex solution in the liquid state, as well as a temperature below that at which the ligand complex is subject to degradation.

By virtue of its heterogeneous, solid character, the specified catalyst is readily applied in either a stirred tank or a fixed or fluid bed reactor, and to either a batch or continuous mode of operation. In other respects, the process of the invention is suitably carried out using procedures and equipment conventionally applied to hydroformylation processes. Following the hydroformylation reaction, the catalyst is readily removed from the product by gravity settling, centrifugation, filtration and/or one or more other solid-liquid separation techniques. The organic product mixture is recovered and treated, as desired, for product separation and purification, reactant separation and recycle, etc.

The invention is further described with reference to the following examples, which illustrate certain preferred embodiments of the invention and are not intended to limit its broader scope.

EXAMPLE 1

Catalyst preparation

A supported aqueous phase catalyst according to the invention was prepared, in which the solid support was a controlled pore glass CPG-240 (obtained from Electro-Nucleonics, Inc., and characterized by a 120/200 mesh size, a mean pore diameter of 237 Å$\pm$4.3%, a pore volume of 0.95 ml/g, and a surface area of 77.5 m$^2$/g) and the organometallic complex was hydridocarbonyl tris(sodiumtriphenylphosphine trisulfonate) rhodium(I).

Triphenylphosphine trisulfonate was first synthesized by the following procedures. Triphenylphosphine, 8 grams, was vacuum deareated, blanketed with argon, and cooled to 10° C. in a water bath. Then, 13.7 ml of sulfuric acid (95%) were added dropwise with vigorous stirring. (Unless otherwise indicated, concentrations noted herein are given in percent by weight.) Stirring was continued until complete dissolution. A mixture of 10.8 ml of 30% sulfur trioxide in sulfuric acid and 16.6 ml of 99% sulfur trioxide was added slowly dropwise with stirring. The temperature of the water bath was allowed to increase to 20.5° C. over a seven-hour period. After twelve hours, the reaction was quenched by cooling to 6° C., followed by the dropwise addition of 200 ml deareated cooled water. The resulting aqueous solution was extracted two times with 50 grams each of tributylphosphate. The tributylphosphate layer was neutralized by vigorous stirring with 50% sodium hydroxide in water in an ice bath with agitation under an argon atmosphere. The resultant sludge was washed five times with 100 ml of ethyl ether per washing and then vacuum dried. The sludge was then dissolved in 75 ml of distilled water. Addition of 75 ml absolute methanol generated a brown precipitate, which was removed by filtration. The mother liquor was evaporated under vacuum to give high purity sodium triphenylphosphine tri-meta-sulfonate. Yield was 29%, calculated on triphenylphosphine starting material.

Hydridocarbonyl tris(sodiumtriphenylphosphine trisulfonate) rhodium(I) was then prepared from the triphenylphosphine trisulfonate. For this purpose, 50 milligrams (mg) of acetylacetonate dicarbonyl rhodium(I) were added to a vigorously stirred one ml deaerated solution of 400 mg of the sodium triphenylphosphine trisulfonate in water. After complete dissolution, stirring was continued for six hours under an atmosphere of hydrogen and carbon monoxide (a 1:1 molar ratio of $H_2$ to CO) at room temperature and atmospheric pressure. The resulting solution was filtered under nitrogen to remove small amounts of rhodium metal present. Then 8 ml of absolute ethanol saturated with a mixture of $H_2/CO$ (1:1 by mol) were added to precipitate the desired complex. The mixture was centrifuged to recover the precipitate, which was then washed with absolute ethanol and vacuum dried. Analysis indicated a high purity hydridocarbonyl tris(sodiumtriphenylphosphine trisulfonate) rhodium(I) complex, with no detectable phosphine oxide.

This complex was next loaded onto the solid catalyst support. The solid complex was dissolved in 25 ml of deaerated water, along with 410 mg of triphenylphosphine trisulfonate, and the resulting solution was poured into 8.8 grams of the CPG-240 solid, which had been previously deaerated and argon blanketed. The slurry obtained was degassed under vacuum and blanketed with argon at one atmosphere. Finally, the slurry was dried under vacuum to a water content of about 2.9% w, based on the weight of the dry solid (or, equivalently, about 2.8% w based on total catalyst weight. The resulting material was stored at atmospheric pressure and room temperature under an atmosphere of $H_2$ and CO (1.1 mol).

EXAMPLE 2

Water addition

A twenty milligram quantity of the catalyst from Example 1 was loaded into a microreactor immersed in a thermostatic bath at 30° C. After evacuation under vacuum, the catalyst was allowed to adsorb water. Communication was established between the reactor and the vapor space of a flask of degassed water, which was also immersed in the 30° C. thermostatic bath. After ninety minutes of exposure to the water vapor, argon was admitted into the system and the reactor was closed.

The hydrated catalyst of Example 2 contained about 8.5% w of water calculated on the weight of the dry solid (about 7.5% w calculated on total weight of the catalyst).

EXAMPLE 3

Hydroformylation of oleyl alcohol

Under dry nitrogen atmosphere, the microreactor was loaded with 0.10 grams of the catalyst prepared in Example 1 and 0.10 grams of oleyl alcohol (in a 25% by volume solution in cyclohexane). The reactor was then flushed with a $H_2/CO$ mixture (1:1 by mol) and pressurized with the same $H_2/CO$ mixture to 825 psig. The reactor was heated to 100° C. and maintained at that temperature with stirring for 5.5 hours. Analysis of the product showed a conversion of 96.6% of the oleyl alcohol and confirmed that the double bond of the alcohol had undergone hydroformylation.

EXAMPLE 4

Evaluation of rhodium leaching

The slurry of reactants, products and catalyst in the reactor at the completion of the hydroformylation reaction of Example 3 was filtered to separate out the supported catalyst particles. To the filtered liquid was added sufficient additional oleyl alcohol to raise its concentration from 3.4% to 46%. For a period of nine hours, the resulting solution was then subjected to the same temperature, $H_2/CO$ pressure and stirring conditions as the hydroformylation reaction mixture of Example 3. No increase in the concentration of aldehydes was observed.

To further evaluate the possibility of the loss of rhodium from the catalyst during the reaction of Example 3, the cyclohexane solvent was evaporated from the solution. To the oleyl alcohol reactant and its hydroformylation products remaining after the evaporation of the cyclohexane, 0.10 ml of 1-hexene was added. The reactor was flushed with hydrogen and pressurized at 60 psig with hydrogen. The temperature was raised to 100° C. and the reactor contents stirred under hydrogen for 2 hours. No hydrogenation of the 1-hexene was detected, indicating no zero valent rhodium metal in the system.

These experiments indicate that the catalytically active rhodium complex remains effectively immobilized on the solid surface of the catalyst during the hydroformylation process of this invention.

EXAMPLES 5-8

A series of other catalysts, suitable for use in the invention, were prepared following the procedures of Examples 1 and 2, but varying the duration of their exposure to water vapor during hydration of the impregnated support and, thus, the quantity of water in the aqueous phase of the finished catalyst. The parameters for the hydration step in the preparation of each of the catalysts of Examples 1, 2, and 5-8 are shown in the following Table. Water content of the finished catalyst is given in terms of percent by weight (% w) of water, relative to weight of the total catalyst.

| Example No. | Duration of Exposure to Water Vapor (Hours) | Water Content of Finished Catalyst (% w) |
| --- | --- | --- |
| 1 | 0 | 2.8 |
| 5 | 0.75 | — |
| 2 | 1.5 | 7.5 |
| 6 | 3 | — |
| 7 | 6 | 31 |
| 8 | 6.5 | — |

EXAMPLES 9-14

Hydroformylation of 1-octene

In Examples 9-14, each of the supported aqueous phase catalysts prepared as described in Examples 1, 5, 2 and 6-8, respectively, was evaluated as a catalyst for the process of this invention, specifically for catalysis of the hydroformylation of 1-octene.

For each of the hydroformylation reactions, 0.40 ml of a solution of 1-octene (20% by volume in degassed cyclohexane) was introduced into the microreactor containing the finished catalyst. The reactor was flushed with a $H_2/CO$ mixture (1:1 mol), pressurized with 750 psig of this $H_2/CO$ mixture and stirred in an oil bath at 70° C. After five hours, the reaction was stopped and the product mixture analyzed to determine the conversion of 1-octene to $C_9$ aldehyde, and the ratio of linear to branched carbon chain $C_9$ aldehydes. Results of the hydroformylation reactions are summarized in the following table.

| Example No. | Applying Catalyst of Example No. | Octene Conversion (%) | Ratio of Linear to Branched Aldehydes |
|---|---|---|---|
| 9 | 1 | 10 | 2.1 |
| 10 | 5 | 38.5 | 2.9 |
| 11 | 2 | 62.5 | 2.7 |
| 12 | 6 | 45 | 2.85 |
| 13 | 7 | 5.9 | 2.5 |
| 14 | 8 | 4.1 | 2.5 |

EXAMPLES 15–18

In a manner similar to that described in Example 9, other olefinically unsaturated reactant compounds were hydroformylated in the presence of the catalyst described in Example 1. The olefinic reactant was introduced as a 20% by volume solution in cyclohexane in Example 15 and as a 50% by volume solution in Examples 16, 17 and 18. Other reaction conditions and the results for each of these examples are summarized in the following Table.

| Example No. | Olefinically Unsaturated Reactant | Grams Rh Per Gram Reactant | $H_2/CO$ Pressure (psig) | Temperature (°C.) |
|---|---|---|---|---|
| 15 | 1-octene | 0.001 | 725 | 95 |
| 16 | c-jasmone | 0.0002 | 750 | 100 |
| 17 | dicyclopentadiene | 0.0002 | 750 | 100 |
| 18 | dicyclopentadiene | 0.0002 | 750 | 100 |

| Example No. | Reaction Time (Hours) | Conversion (%) | Comments |
|---|---|---|---|
| 15 | 3 | 98.7 | normal/branched ratio = 1.8 |
| 16 | 5 | 86.5 | 38% aldehydes |
| 17 | 5 | 74.4 | 0.7% dialdehydes |
| 18 | 10 | 100 | 9.2% dialdehydes |

EXAMPLE 19

Rhodium complex solubility in polar solvents

Solubility of the ligand utilized for formation of the rhodium complex, in the catalysts polar solvent, is necessary to the production of a catalyst suitable for use in the process of this invention. A series of experiments was carried out to determine the solubility of the sodium triphenylphosphine tri-m-sulfonate ligand prepared as described in Example 1, in several polar solvents. Solubility of the ligand was measured at 25° C., in terms of the grams of ligand soluble in one gram of water, or ethylene glycol, or glycerol. Results of these experiments, presented in the following Table, show that the ligand is soluble in a variety of different polar solvents.

| Solvent | Ligand Solubility g Ligand per g Solvent |
|---|---|
| water | between 0.52 and 0.85 |
| ethylene glycol | between 0.05 and 0.08 |
| glycerol | about 0.13 |

We claim as our invention:

1. A process for the hydroformylation of a liquid phase olefinically unsaturated organic reactant in the carbon number range from about 3 to about 30, which comprises steps for
    a. contacting and reacting said olefinically unsaturated organic reactant with a mixture of carbon monoxide and hydrogen, under hydroformylation conditions, in the presence of an effective amount of a heterogeneous catalyst comprising a solid surface having immobilized thereon a solution of one or more rhodium complexes in a polar solvent, said solution characterized as essentially immiscible with said olefinically unsaturated organic reactant phase, and
    b. separating the catalyst from the resulting reaction mixture.

2. The process of claim 1, wherein the polar solvent contains a quantity of water which is at least equal to that corresponding to the water of hydration of the one or more rhodium complexes.

3. The process of claim 2, wherein the polar solvent is predominantly water.

4. The process of claim 3, wherein the polar solvent consists essentially of water.

5. The process of any one of claims 1–4, wherein the solid surface is provided by a porous solid.

6. The process of claim 5, wherein the pores of the porous solid are predominantly of a diameter greater than about 20 Å.

7. The process of claim 6, wherein the quantity of polar solvent in the immobilized catalyst solution is about 10 percent or more, relative to the quantity of the rhodium complex present.

8. The process of claim 7, wherein the solution of one or more rhodium complexes in a polar solvent is immobilized on the external and pore surfaces of the porous solid by a method which comprises impregnating the porous solid with a solution of the rhodium complexes in a solvent, removing said solvent from the impregnated solution by evaporation to deposit the complexes on the surfaces, contacting the solid surfaces with polar solvent in the vapor phase, and condensing the polar solvent on the surfaces to dissolve in whole or part the deposited rhodium complexes.

9. The process of claim 8, wherein the olefinically unsaturated organic reactant is an alkene.

10. The process of claim 6, wherein the pores of the porous solid are of relatively uniform size.

11. A process for the hydroformylation of a liquid phase olefinically unsaturated organic reactant in the carbon number range from about 3 to about 30, which comprises steps for
    a. contacting and reacting said olefinically unsaturated organic reactant with a mixture of carbon monoxide and hydrogen, under hydroformylation conditions, in the presence of an effective amount of a heterogeneous catalyst comprising a solid surface having immobilized thereon a solution of one or more sulfonated phosphine complexes of rhodium in a polar solvent, said solution characterized as essentially immiscible with said olefinically unsaturated organic reactant phase, and
    b. separating the catalyst from the resulting reaction mixture.

12. The process of claim 11, wherein the polar solvent contains a quantity of water which is at least equal to that corresponding to the water of hydration of the one or more rhodium complexes.

13. The process of claim 12, wherein the polar solvent is predominantly water.

14. The process of claim 13, wherein the polar solvent consists essentially of water.

15. The process of any one of claim 11-14, wherein the solid surface is provided by a porous solid.

16. The process of claim 15, wherein the pores of the porous solid are predominantly of a diameter greater than about 20 Å.

17. The process of claim 16, wherein the pores of the porous solid are of relatively uniform size.

18. The process of claim 16, wherein the quantity of polar solvent in the immobilized catalyst solution is about 10 percent or more, relative to the quantity of the rhodium complex present.

19. The process of claim 18, wherein the solution of one or more rhodium complexes in a polar solvent is immobilized on the external and pore surfaces of the porous solid by a method which comprises impregnating the porous solid with a solution of the rhodium complexes in a solvent, removing said solvent from the impregnated solution by evaporation to deposit the complexes on the surfaces, contacting the solid surfaces with polar solvent in the vapor phase, and condensing the polar solvent on the surfaces to dissolve in whole or part the deposited rhodium complexes.

20. A process for the hydroformylation of a liquid phase olefinically unsaturated organic reactant in the carbon number range from about 3 to about 30, which comprises steps for
   a. contacting and reacting with olefinically unsaturated organic reactant with a mixture of carbon monoxide and hydrogen, under hydroformylation conditions, in the presence of an effective amount of a heterogeneous catalyst comprising a porous solid, wherein the pores are predominantly of a diameter greater than about 20 Å, having immobilized on the external and pore surfaces thereof a solution of one or more sulfonated phosphine complexes of rhodium in an aqueous solvent, said solution characterized as essentially immiscible with said olefinically unsaturated organic reactant phase, and
   b. separating the catalyst from the resulting reaction mixture.

21. The process of claim 20, wherein the olefinically unsaturated organic reactant is an alkene.

22. The process of claim 21, wherein the quantity of polar solvent in the immobilized catalyst solution is about 10 percent or more, relative to the quantity of the rhodium complex present.

23. The process of claim 21, wherein the pores of the porous solid are of relatively uniform pore size.

24. The process of claim 22, wherein the solution of one or more rhodium complexes in a pole solvent is immobilized on the external and pore surfaces of the porous solid by a method which comprises impregnating the porous solid with a solution of the rhodium complexes in a solvent, removing said solvent from the impregnated solution by evaporation to deposit the complexes on the surfaces, contacting the solid surfaces with polar solvent in the vapor phase, and condensing the polar solvent on the surfaces to dissolve in whole or part the deposited rhodium complexes.

25. The process of claim 19, wherein the olefinically unsaturated organic reactant is an alkene.

26. The process of any one of claims 1, 11, 20 and 21, wherein step (a) is carried out at a temperatures in the range from about 50° to 250° C. and at a pressure in the range from about 1 to 200 atm.

* * * * *